US009351633B2

(12) United States Patent
Tydlaska et al.

(10) Patent No.: US 9,351,633 B2
(45) Date of Patent: *May 31, 2016

(54) WIRELESS CONTROL OF LARYNGOSCOPE SYSTEM

(75) Inventors: Jay (Jason) Tydlaska, Fort Worth, TX (US); Amy Sheppard, Fort Worth, TX (US)

(73) Assignee: Magaw, L.L.C., Fort Worth, TX (US)

( * ) Notice: Subject to any disclaimer, the term of this patent is extended or adjusted under 35 U.S.C. 154(b) by 691 days.

This patent is subject to a terminal disclaimer.

(21) Appl. No.: 13/374,985

(22) Filed: Jan. 27, 2012

(65) Prior Publication Data
US 2012/0169481 A1 Jul. 5, 2012

Related U.S. Application Data

(62) Division of application No. 12/750,784, filed on Mar. 31, 2010, now Pat. No. 8,864,657.

(60) Provisional application No. 61/165,091, filed on Mar. 31, 2009, provisional application No. 61/437,010, filed on Jan. 28, 2011.

(51) Int. Cl.
*A61B 1/267* (2006.01)
*A61B 1/00* (2006.01)
*A61M 16/04* (2006.01)

(52) U.S. Cl.
CPC ............. *A61B 1/267* (2013.01); *A61B 1/00052* (2013.01); *A61B 1/00101* (2013.01); *A61B 1/00105* (2013.01); *A61M 16/0488* (2013.01); *A61M 2205/3569* (2013.01); *A61M 2205/3592* (2013.01); *A61M 2205/502* (2013.01); *A61M 2209/082* (2013.01)

(58) Field of Classification Search
CPC ................................. A61B 1/267; G05B 11/01
See application file for complete search history.

(56) References Cited

U.S. PATENT DOCUMENTS

| 2,646,036 | A | * | 7/1953 | Allyn | A61B 1/267 403/27 |
| 4,185,639 | A | * | 1/1980 | Linder | A61M 16/0488 128/200.26 |
| 4,579,108 | A | * | 4/1986 | Bauman | A61B 1/267 600/186 |
| 4,832,020 | A | * | 5/1989 | Augustine | A61M 16/0488 128/207.14 |
| 4,834,077 | A | * | 5/1989 | Sun | A61B 1/00142 600/186 |
| 4,979,499 | A | * | 12/1990 | Sun | A61B 1/00142 600/186 |

(Continued)

FOREIGN PATENT DOCUMENTS

| WO | 9855170 | 12/1998 |
| WO | 02051304 | 7/2002 |

(Continued)

*Primary Examiner* — Christian Sevilla
(74) *Attorney, Agent, or Firm* — Decker Jones, P.C.; Brian K. Yost; Geoff Mantooth

(57) ABSTRACT

A Laryngoscope system for controlling and monitoring characteristics associated with airway management and a remote access unit continuously interfacing through instant wireless private direct connectivity to a laryngoscope. The system also includes a plurality of sensors and controllers that measure and control characteristics and provide the remote unit with measurements and control results. In other aspects, the laryngoscope and display unit are sensitive to movement and may power on and off with motion or absence of motion. In another aspect, the laryngoscope is capable of wirelessly communicating with the screen for command and control of the Laryngoscope and laryngoscope system.

29 Claims, 13 Drawing Sheets

(56) References Cited

U.S. PATENT DOCUMENTS

| | | | | |
|---|---|---|---|---|
| 5,487,607 A * | 1/1996 | Makita | A61B 5/01 | 374/121 |
| 5,743,849 A * | 4/1998 | Rice | A61B 1/267 | 600/186 |
| 5,766,202 A * | 6/1998 | Jones | A61M 29/00 | 604/270 |
| 5,800,344 A * | 9/1998 | Wood, Sr. | A61B 1/267 | 600/185 |
| 5,810,770 A * | 9/1998 | Chin | A61M 3/0258 | 604/65 |
| 5,846,186 A | 12/1998 | Upsher | | |
| 6,001,066 A * | 12/1999 | Canfield | G01J 5/0022 | 374/E13.003 |
| 6,142,144 A * | 11/2000 | Pacey | A61B 1/2676 | 128/200.26 |
| 6,146,402 A * | 11/2000 | Munoz | A61B 1/0607 | 606/194 |
| 6,248,061 B1 * | 6/2001 | Cook, Jr. | A61B 1/267 | 600/187 |
| 6,354,993 B1 * | 3/2002 | Kaplan | A61B 1/07 | 600/188 |
| 6,494,826 B1 * | 12/2002 | Chatenever | A61B 1/00188 | 600/112 |
| 6,543,447 B2 * | 4/2003 | Pacey | A61B 1/05 | 128/200.26 |
| 6,569,089 B1 * | 5/2003 | Covington | A61B 1/0669 | 600/199 |
| 6,655,377 B2 * | 12/2003 | Pacey | A61B 1/2676 | 128/200.26 |
| 6,666,819 B2 * | 12/2003 | Heine | A61B 1/267 | 600/193 |
| 6,817,973 B2 * | 11/2004 | Merril | A61B 19/22 | 600/103 |
| 6,840,903 B2 * | 1/2005 | Mazzei | A61B 1/267 | 600/185 |
| 6,843,769 B1 * | 1/2005 | Gandarias | A61B 1/0676 | 600/185 |
| 6,890,298 B2 * | 5/2005 | Berci | A61B 1/00188 | 600/112 |
| 7,044,909 B2 * | 5/2006 | Berci | A61B 1/00188 | 600/185 |
| D534,652 S * | 1/2007 | McGrath | D24/135 | |
| 7,347,863 B2 * | 3/2008 | Rothe | A61B 17/0401 | 606/139 |
| D590,501 S | 4/2009 | McGrath | | |
| 7,695,433 B2 * | 4/2010 | Simons | A61B 1/267 | 600/185 |
| 8,187,180 B2 * | 5/2012 | Pacey | A61B 1/00142 | 600/186 |
| 2001/0014768 A1 * | 8/2001 | Kaplan | A61B 1/07 | 600/188 |
| 2002/0022769 A1 * | 2/2002 | Smith | A61B 1/00052 | 600/188 |
| 2002/0082478 A1 * | 6/2002 | McGrath | A61B 1/267 | 600/193 |
| 2003/0078476 A1 * | 4/2003 | Hill | A61B 1/00052 | 600/160 |
| 2003/0100819 A1 * | 5/2003 | Newman | A61B 1/00052 | 600/300 |
| 2004/0127770 A1 * | 7/2004 | McGrath | A61B 1/267 | 600/193 |
| 2006/0004258 A1 * | 1/2006 | Sun | A61B 1/00052 | 600/160 |
| 2006/0020166 A1 * | 1/2006 | Berall | A61B 1/267 | 600/121 |
| 2006/0020176 A1 * | 1/2006 | Berall | A61B 1/267 | 600/300 |
| 2006/0165152 A1 * | 7/2006 | Walker | G01J 5/021 | 374/158 |
| 2006/0276693 A1 * | 12/2006 | Pacey | A61B 1/00142 | 600/188 |
| 2006/0276694 A1 * | 12/2006 | Acha Gandarias | A61B 1/015 | 600/194 |
| 2007/0179342 A1 * | 8/2007 | Miller | A61B 1/267 | 600/188 |
| 2007/0195539 A1 * | 8/2007 | Birnkrant | A61B 1/00016 | 362/458 |
| 2007/0197873 A1 * | 8/2007 | Birnkrant | A61B 1/00016 | 600/160 |
| 2007/0299313 A1 * | 12/2007 | McGrath | A61B 1/00087 | 600/186 |
| 2008/0045801 A1 * | 2/2008 | Shalman | A61B 1/267 | 600/193 |
| 2008/0177146 A1 * | 7/2008 | Chen | A61B 1/267 | 600/185 |
| 2008/0177147 A1 * | 7/2008 | Simons | A61B 1/267 | 600/186 |
| 2008/0177148 A1 * | 7/2008 | Chen | A61B 1/05 | 600/188 |
| 2008/0249355 A1 * | 10/2008 | Birnkrant | A61B 1/00105 | 600/112 |
| 2008/0249370 A1 * | 10/2008 | Birnkrant | A61B 1/00105 | 600/188 |
| 2009/0299146 A1 * | 12/2009 | McGrath | A61B 1/00096 | 600/188 |
| 2011/0245609 A1 * | 10/2011 | Laser | A61B 1/00052 | 600/109 |
| 2011/0319718 A1 * | 12/2011 | Hakanen | A61B 1/06 | 600/193 |
| 2012/0149980 A1 * | 6/2012 | Pacey | A61B 1/00082 | 600/109 |
| 2012/0316398 A1 * | 12/2012 | Ashcraft | A61B 1/267 | 600/188 |

FOREIGN PATENT DOCUMENTS

| | | |
|---|---|---|
| WO | 2004/096032 | 11/2004 |
| WO | 2004096031 | 11/2004 |
| WO | 2004096032 | 11/2004 |
| WO | 2008138119 | 11/2008 |
| WO | 2010100497 | 9/2010 |

* cited by examiner

WIRELESS CONTROL OF LARYNGOSCOPE SYSTEM

CROSS REFERENCE TO RELATED APPLICATIONS

This application is a divisional which claims the benefit of US Published Application US 2010/0249513 A1 filed on Mar. 31, 2010, which claims the benefit of PPA No. 61/165,091, filed on Mar. 31, 2009 referenced by incorporation herein which claims the benefit of PPA 61/427,010 filed Jan. 28, 2011 by the present inventor.

DESCRIPTION OF THE PRIOR ART

Over 20 million intubation procedures are performed each year in the United States either as a routine part of surgery or in emergency situations resulting from trauma, cardiopulmonary arrest or other disease processes. In an intubation procedure, it is necessary to insert an endotracheal tube (ET tube) in order to maintain a patient's respiratory function. The tube is inserted into a patient's trachea via either the mouth or nasal tract so that the airway remains open and oxygen reaches the patient's lungs.

Practitioners use an instrument known as a laryngoscope to help in the placement of the ET tube. This instrument typically comprises a handle, a blade, and a light. The practitioner uses the device to move the tongue and epiglottis to one side so that the airway may be properly identified. Once the airway is properly identified, the practitioner inserts the tube with one hand while holding the laryngoscope with the other. In a small percentage of patients, the airway cannot be identified with the laryngoscope alone. With these patients, practitioners sometimes use a device known as a "bougie". This bougie is a small diameter flexible cylinder of metal, plastic or other material that may serve as a guide for placement of a larger ET tube.

The laryngoscope predominantly used today to accomplish this task was developed in the 1940's. When performed by an experienced practitioner, the procedure is usually quick and uneventful. However, even in the hands of well skilled individuals, there is still an unacceptable number of occurrences in which placement of the endotracheal tube is difficult or impossible resulting in an inability to provide the patient with oxygen leading to death or injury. Difficulty in placing the endotracheal tube may be due to trauma, abnormal anatomy, disease processes or for unknown and unpredictable reasons.

Over the years, there have been many attempts to improve upon the design of the original laryngoscope, but those attempts have been largely unsuccessful as evidenced by the continued use today of virtually the same device developed in the 1940's. More recently due to advances in miniaturization of technology, devices have been developed known as video laryngoscopes that greatly improve the ability to adequately locate the vocal cords and appropriately place the endotracheal tube. These devices are generally constructed with a small camera placed at the distal end of the laryngoscope and the image obtained by that camera is viewed on a remote monitor. However, these devices are expensive and often inconvenient to use. Moreover, prior art devices still fail to offer a solution to the difficult intubations in which a bougie is necessary.

What is needed is an inexpensive, sanitary, easy to use laryngoscope system that may be used in all situations, including the most difficult intubations in the most challenging environments.

SUMMARY OF THE INVENTION

It is an object of the invention to provide an inexpensive, sanitary, easy to use laryngoscope system that may be used in all situations, including most difficult intubations in the most challenging environments.

The present invention generally provides a laryngoscope capable of being connected to a monitor and power source, said laryngoscope being comprised of a handle, an arm, a camera, a light, and a disposable sheath; wherein the sheath is slideably and removably coupled to the arm; the sheath being further comprised of a canal capable of being threaded with a bougie; the handle being further comprised of a remote ejection element mechanically connected to a spring element capable of ejecting the sheath from the arm; the arm being removably coupled to the handle. The system is further comprised of a display device, and an IV pole attachment. The sheath may be remotely ejected by depressing a thumb ejector switch on the handle which releases a clasp at the coupling point and further releases a spring element held in compression which, upon release, forcibly moves the sheath along the length of the arm, such that the sheath becomes detached from the arm. The sheath is further comprised of a small canal at least partially running along the outside length that serves as a guide for the bougie. With the laryngoscope properly placed, the practitioner may thread a bougie through the sheath's bougie canal into the airway and use this bougie as a guide for the ET tube.

The laryngoscope is further comprised of a light and a camera. The lens of this camera is located at the distal end of the arm and the signal is transmitted either wirelessly or through a cord to the display device. The light is also located at the distal end of the arm. The cord further transmits power from a power source to the light and camera. In one embodiment of the present invention, the camera is located in the arm of the camera with the lens positioned near the body of the camera. In another embodiment, the body of the camera is located in the handle and communicates with the lens through a cable. In still another embodiment of the present invention, the image collected by the lens is reflected on a mirror or prism.

The display unit is comprised of a container, a screen, and a battery. The container is configured such that it may be removably coupled to an IV pole attachment or sit upright when not attached to the IV pole attachment.

The IV pole is conventional and commercially available. The IV pole attachment is comprised of an attachment receiver that allows the user to quickly attach and separate the display unit from the IV Pole attachment, an IV clamp with a "C" shaped opening, and a laryngoscope storage receptacle.

In one aspect of the present invention, the laryngoscope is comprised of a heating element.

In one aspect of the present invention, the laryngoscope is capable of being motion activated such that the laryngoscope is powered on upon movement.

In another aspect of the present invention, the laryngoscope is capable of being motion activated such that the laryngoscope is powered off when no movement is detected for a predetermined period of time.

In one aspect of the present invention, the screen is capable of being motion activated such that the screen is powered on upon movement.

In another aspect of the present invention, the screen is capable of being motion activated such that the screen is powered off when no movement is detected for a predetermined period of time.

In another aspect of the present invention, the arm is removably coupled to the handle.

In another aspect of the present invention, a user using the ejection element may eject the sheath without touching the sheath.

In another aspect of the present invention, the display unit is comprised of a stand such that said unit is capable of standing upright.

In another aspect of the present invention, the laryngoscope is capable of wirelessly communicating with the screen.

DESCRIPTION OF THE PREFERRED EMBODIMENT

Figure 1:
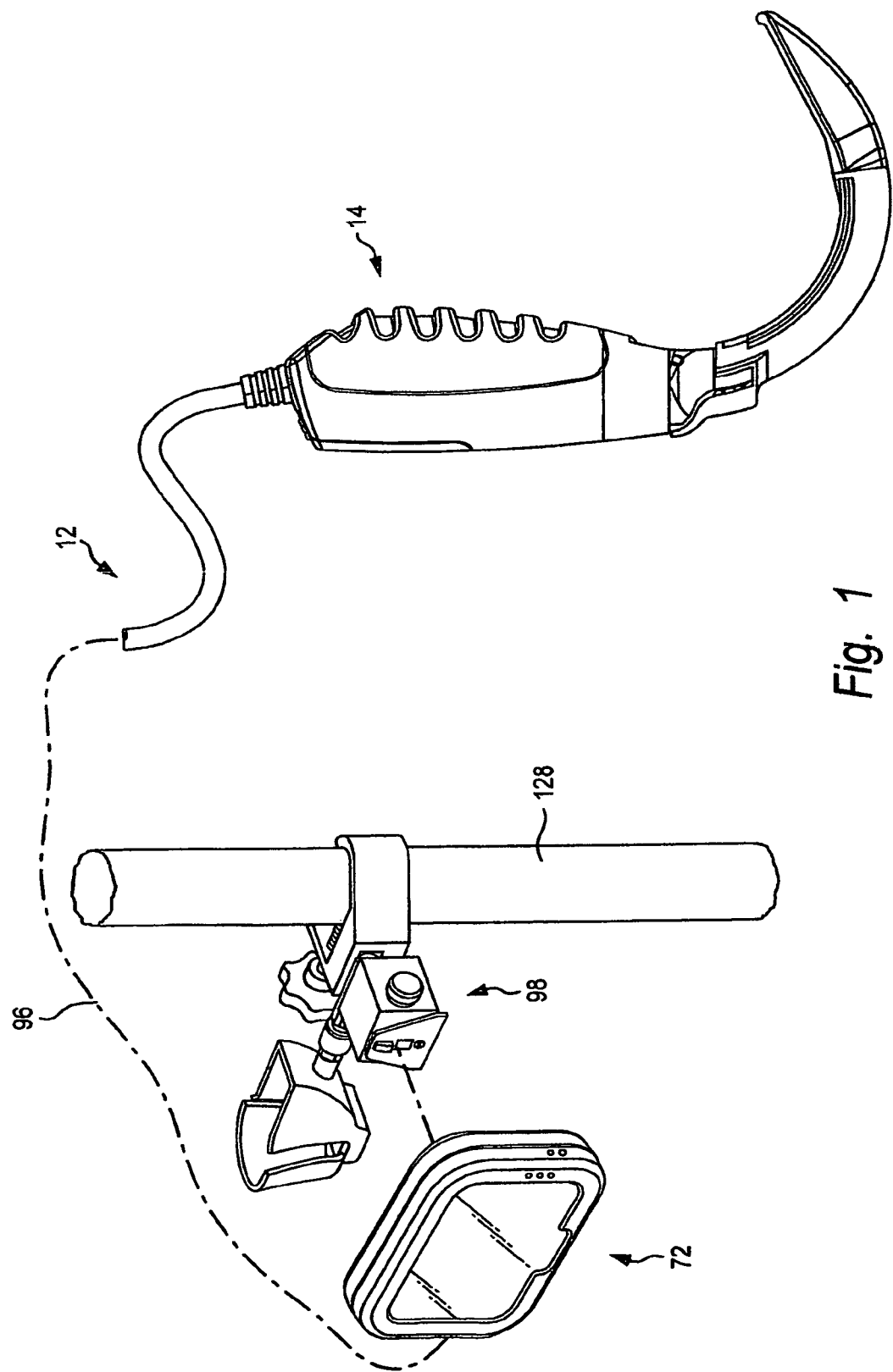
FIG. 1 is a side perspective view of the laryngoscope system in accordance with a preferred embodiment.

Referring to FIGS. 1-15 there is shown a laryngoscope system 12 of the present invention. This laryngoscope system 12 is generally comprised of a laryngoscope 14, a display unit 72, and an IV pole attachment 98 capable of being coupled to an IV pole 128.

Figure 2A:
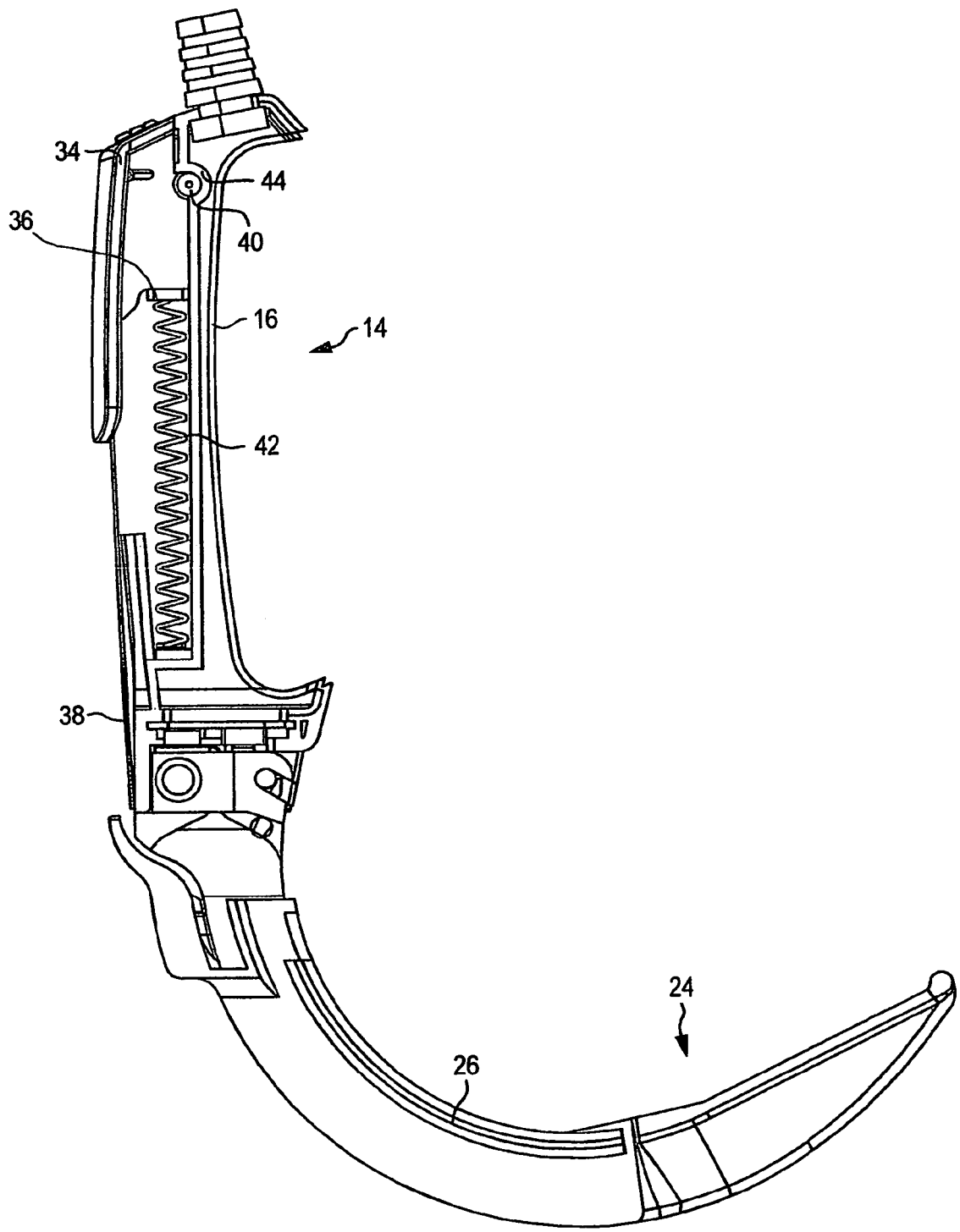
FIG. 2A is an isometric cut-away right side view of the laryngoscope in the open position with the arm and sheath attached in accordance with a preferred embodiment.
Figure 2B:
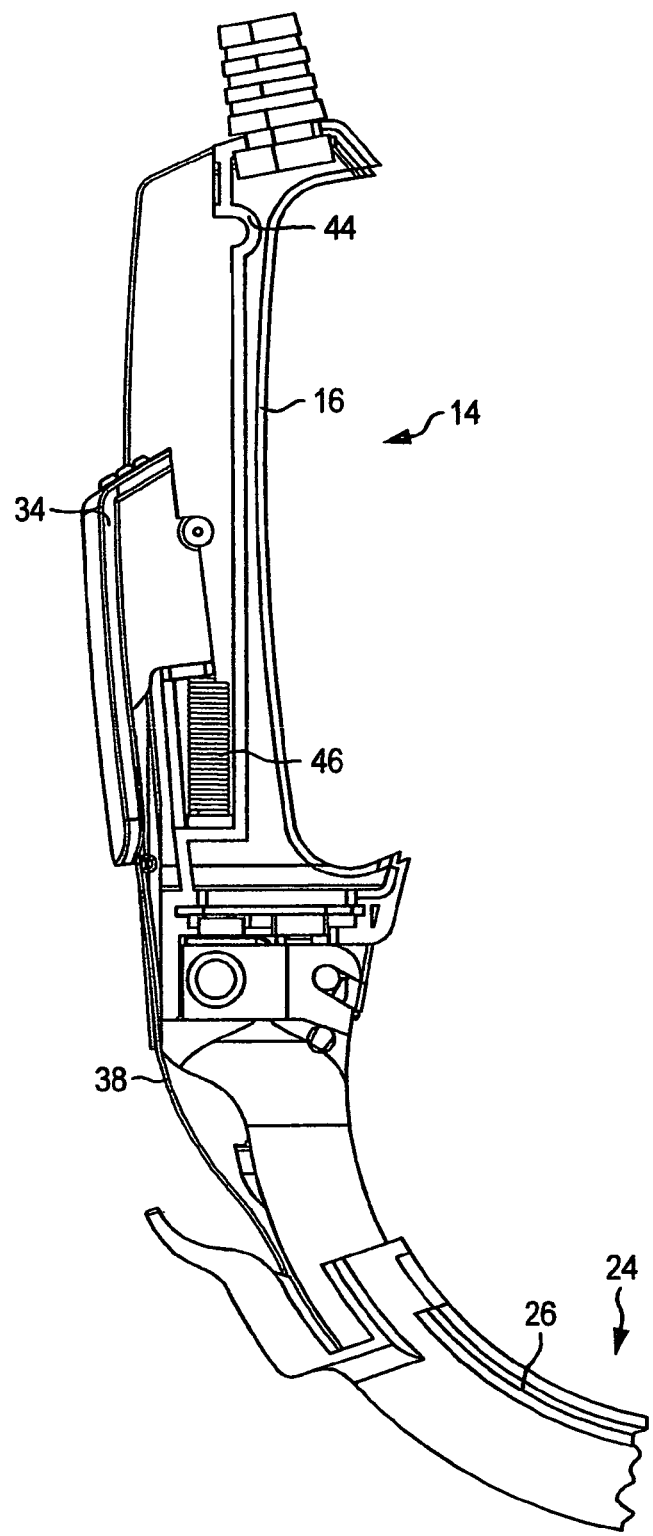
FIG. 2B is an isometric cut-away right side view of the laryngoscope of FIG. 2A with the thumb ejector switch in the extended position.
Figure 3:
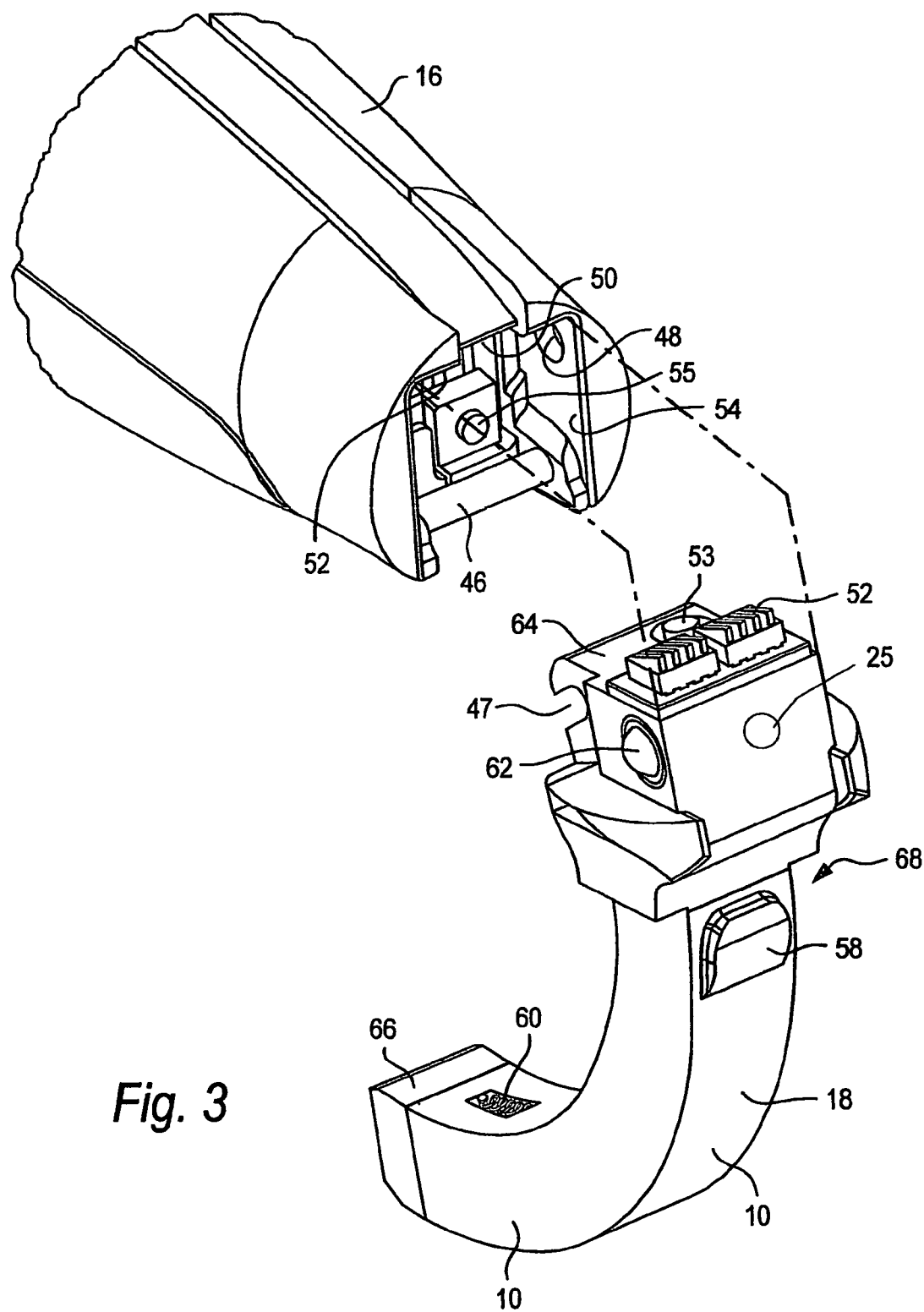
FIG. 3 is an isometric, rear, and side view of the laryngoscope arm and a partial view of the laryngoscope handle, in accordance with a preferred embodiment.
Figure 4:
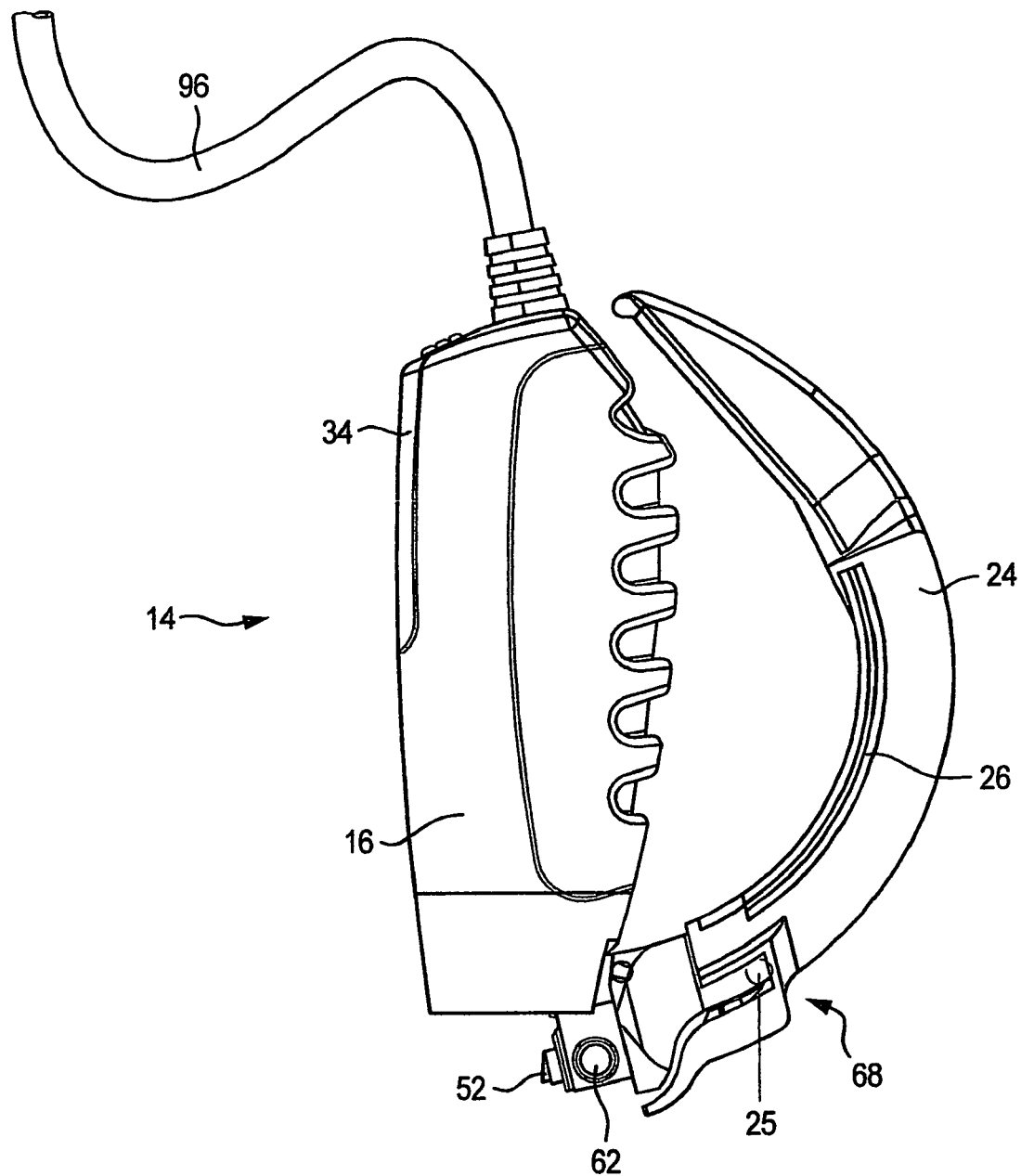
FIG. 4 is an isometric right side view of the laryngoscope with the arm in the closed position in accordance with a preferred embodiment.
Figure 5:
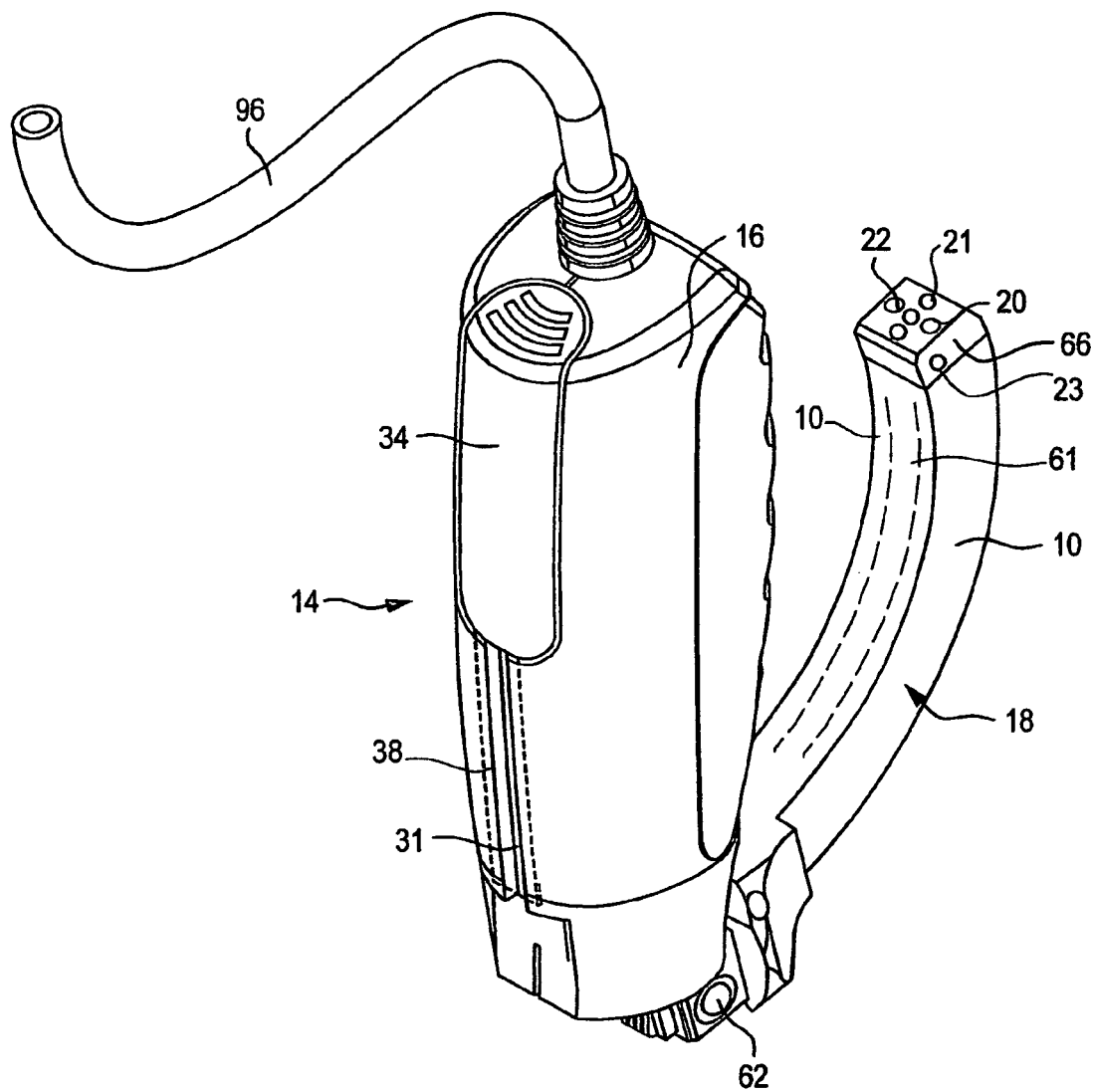
FIG. 5 is an isometric right side and rear view of the laryngoscope with the arm in the closed position without the sheath attached in accordance with a preferred embodiment.
Figure 6:
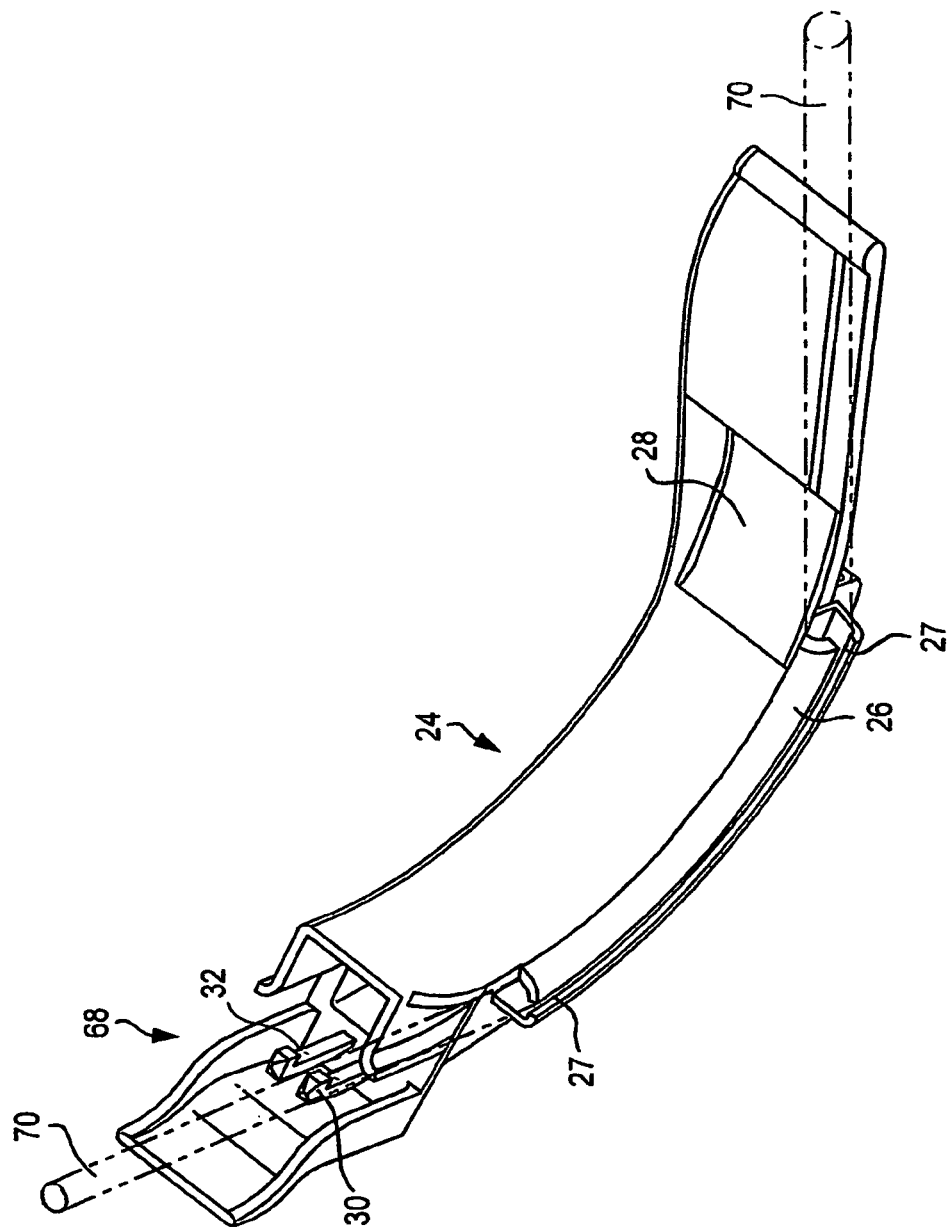
FIG. 6 is an isometric right side, top view of the sheath, in accordance with a preferred embodiment.

Referring to FIGS. 1-6, the laryngoscope 14 of the present invention comprises a handle 16, a curved blade or arm 18, a light 20, a camera 22, and a disposable sheath 24. The handle 16 of the laryngoscope 14 has a curved arm 18 attached. In one aspect of the present invention, the arm 18 is removably coupled to the handle 16. Slideably coupled to the arm 18 is a sheath 24 which snaps into place at a coupling point 68 (FIG. 3). In the preferred embodiment, this sheath 24 is formed from plastic and is at least partially clear so as to allow light emitted from the light 20 to pass through it. Referring to FIG. 6, in the preferred embodiment, the sheath 24 is comprised of a transparent window 28. The sheath 24 has one or more clasps 30 on its proximal end (FIG. 6) which may be removably coupled to the arm 18 at the coupling point 68 (FIG. 3). In one aspect of the present invention, a user, using the thumb ejector switch 34, may eject the sheath 24 without physically touching the sheath 24. Referring to FIGS. 2A, 2B and FIG. 5, the thumb ejector switch 34 is located at the upper end of the handle 16. The thumb ejector switch 34 is comprised of a plunger block 36, an ejection rod 38, and a protrusion 40. The thumb ejector switch 34 is coupled to the ejection rod 38 which is coupled at the top end with the plunger block 36. The plunger block 36 is comprised of the protrusion 40. A return spring 42 is coupled to the thumb ejector switch 34. This return spring 42 maintains the ejection rod 38 in a retracted position as a rest state (FIG. 2A). Above the plunger block 36 is a retaining receptacle 44. This retaining receptacle 44 is structured and arranged such that it is capable of nesting the protrusion 40 and maintains the thumb ejector switch 34 in a rest position and prevents accidental deployment of the ejection rod 38.

Referring to FIGS. 2B, 3, 5 and 6, the sheath 24 may be remotely ejected by depressing the thumb ejector switch 34 (FIG. 2B) on the handle 16 which releases the clasp 30 at a sheath connection ridge 58 located on the arm 18 at the coupling point 68. The thumb injector switch 34, when depressed, travels down a switch channel 31 (FIG. 5). In one embodiment, thumb ejector switch 34 further releases a spring element 60 (FIG. 3) held in compression which, upon release, forcibly moves the sheath 24 along the length of the arm 18, such that the sheath 24 becomes detached from the arm 18. Referring to FIG. 6, in one aspect of a preferred embodiment, the clasp 30 has a score line 32 or thinner layer of material. This score line 32 creates a weakened area in the clasp 30 so that when depressed by the ejection rod 38, the clasp 30 is deformed at the score line 32. In one aspect of the present invention, the clasp 30, after ejection, cannot be returned to its original un-deformed configuration without breaking at the score line 32. Such breaking prevents the sheath 24 from being reused and thus, helps prevent contamination.

In one embodiment of the invention, and as shown in FIG. 6, the sheath 24 is further comprised of a small canal 26 running at least partially along the outside length that serves as a guide for a bougie 70. With the laryngoscope 14 properly placed, the practitioner may thread the bougie 70 through the sheath's bougie canal 26 into the airway and use this bougie 70 as a guide for an ET tube (not shown). As shown in the FIG. 6, in the preferred embodiment, this canal 26 is open on one side 27 such that the bougie 70 may be inserted and removed through this open side 27. This open side 27 permits the user to maintain the laryngoscope 14 in the airway while threading the ET tube over the bougie 70. In this embodiment, the bougie 70 is forced out of the canal 26 through the side opening 27 by the ET tube. In the preferred embodiment, this canal with its open side 27 is "C" shaped. This "C" shape helps maintain the bougie 70 within the canal 26 while still allowing the bougie 70 to be removed through the open side 27. Although the canal 26 of the preferred embodiment is open and forms a "C" shape, the canal 26 need not be open and need not be "C" shaped. Rather, the canal 26 can be closed on the sides so as to completely surround the bougie 70 along its length and can be circular or any other suitable shape.

As best shown in FIG. 5, the laryngoscope 14 also has a light 20 and a camera 22 positioned at the distal end of arm 18 and confined within arm walls 10 beneath a transparent cap 66. This cap 66 is clear and allows light to reach the lens 56 and light generated from the light 20 to exit the arm 18. A lens 56 for this camera 22 is located in the arm 18 and the signal is transmitted through a cord 96 to a display unit 72. While in the preferred embodiment the camera 22 is solid state and does not rely upon mirrors or prisms, the camera 22 may be comprised of a lens 56 that focuses light as an image on a prism. The image may then reflected by the prism to the camera 22.

Figure 12:
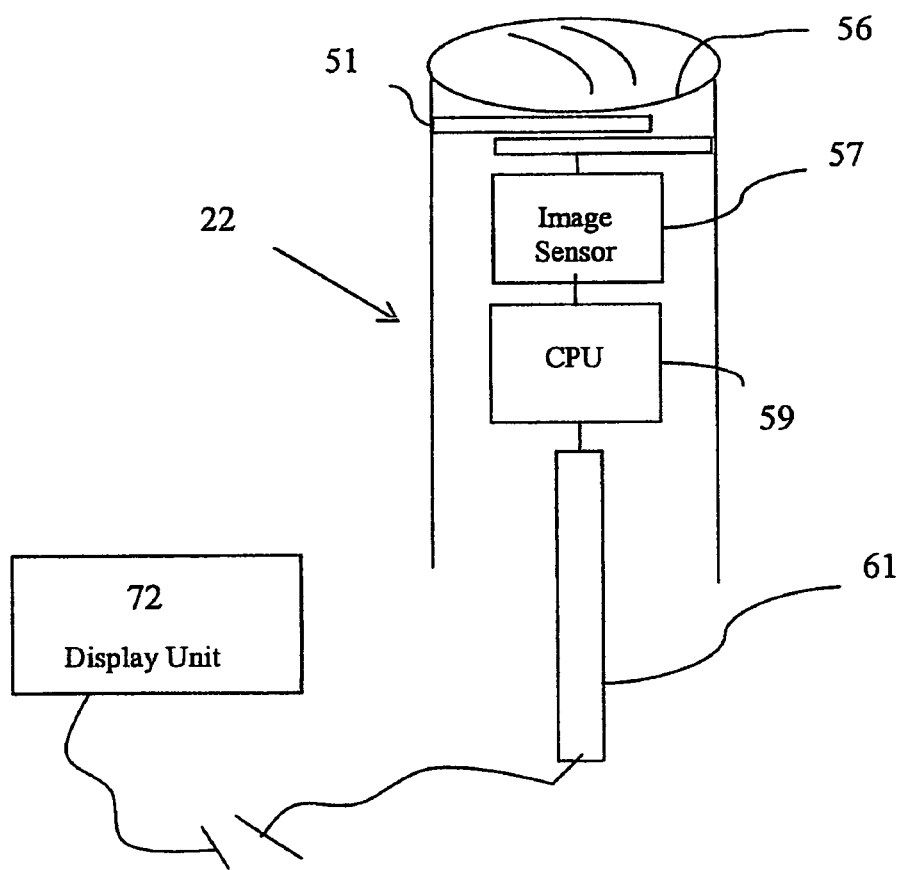
FIG. 12 is a block diagram depicting the camera unit.

Referring to FIGS. 5 & 12, the lens 56 of the camera 22 is also located at the distal end of the arm 18. In another embodiment, the main portion of the camera 22 is located in the handle 16 and communicates with the lens 56 through a fiber optic cable. In one embodiment, the camera 22 transmits the signal directly to the display unit 72 without the use of mirrors and prisms. In the preferred embodiment, the camera 22 is a complementary metal-oxide-semiconductor (CMOS) camera. However, other cameras 22 may be used including those incorporating charge-coupled device (CCD) technology.

In the preferred embodiment, the camera 22 transmits video images to the display unit 72. Referring to FIG. 12, the camera 22 is comprised of a lens 56, a shutter 51, an image sensor 57, a processor or CPU 59, and a flex circuit 61. Images collected by the camera 22 are displayed on the screen 88 of the display unit 72. Although the camera 22 of the preferred embodiment produces video images, it can also generate still images which may also be displayed on the screen 88 of the display unit 72.

Referring to FIG. 5, in the preferred embodiment, the arm 18 is comprised of a heating unit 21. This heating unit 21 heats the light 20 and camera 22 area and prevents the light 20 and camera 22 from developing moisture which may obscure the images gathered by the camera 22. The heating unit 21 is comprised of a thermistor 23 which monitors the temperature of the heating unit 21 and shuts the unit 21 off when a predetermined temperature is reached. In the preferred embodiment, such temperature is approximately 120 degrees Fahrenheit. The arm 18 is further comprised of a flex circuit 61 (FIG. 5). This circuit 61 is capable of supplying power to the camera 22 light 20 and heating unit 21 as well as transmitting information (including images) between the camera 22 and display unit 72. The handle 16 and arm 18 are each further comprised of heater switch 53 and 55. When the laryngoscope 14 is in the folded position, the heater switch 53 and 55 is in the open position and no power to the heater unit 21 is transferred. In this folded position, connectors 52 are also open such that power is not transferred to the light 20, camera 22, and heating unit 21.

As shown in FIGS. 3 & 4, in alternative embodiments, a sheath switch 25 is located on the arm 16. When the sheath 24 is in place and the arm 18 is in the working/engaged position as shown in FIGS. 2A and 2B, power is supplied to the heating unit 21. However, when the sheath 24 is not present, as shown in FIG. 3, or the arm 18 is in the folded/disengaged position depicted in FIG. 4, the heater switch 53, 55 is open, and no power is supplied to the heater unit 21. The sheath switch 25 interrupts power to the handle portion 53 of heater switch 53, 55.

Figure 13:
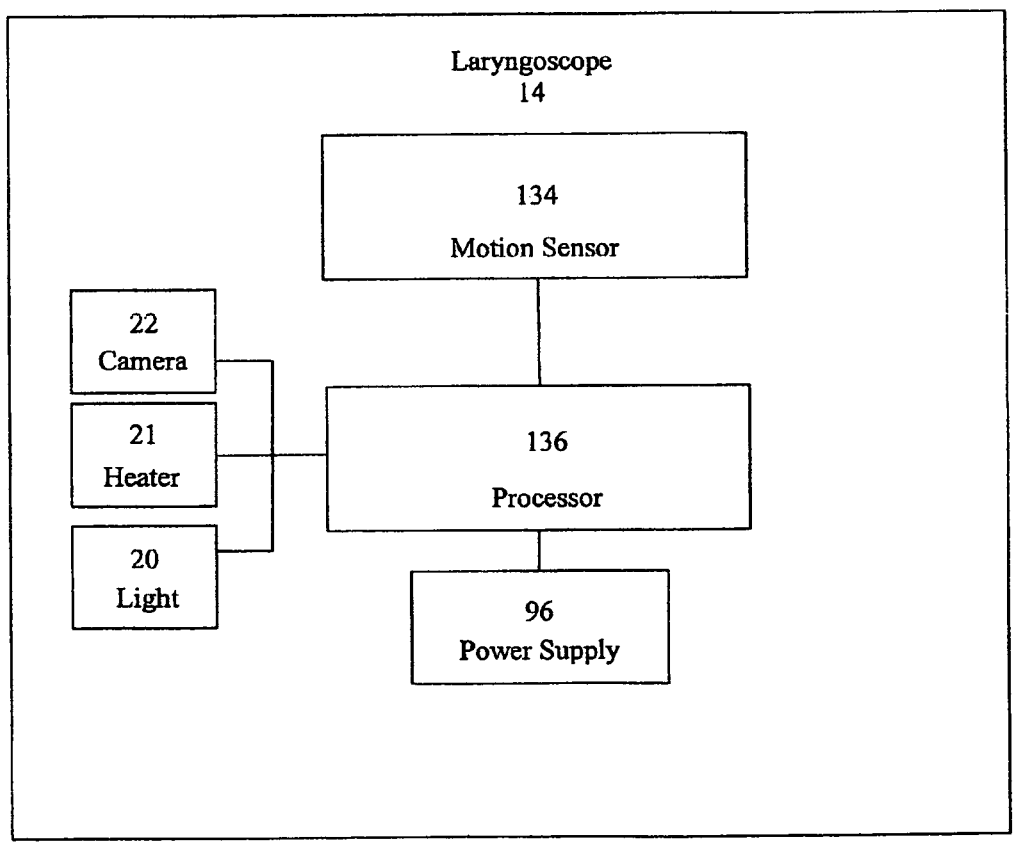
FIG. 13 is a block diagram depicting the laryngoscope motion sensor system.

The cord 96 further transmits power from a power source to the light 20 camera 22 and heating unit 21. Referring to FIG. 13, in one aspect of the present invention the laryngoscope 14 is comprised of a motion sensor 134 and processor 136 that allow the laryngoscope 14 to be motion activated such that the laryngoscope 14 is powered on upon a predetermined threshold of movement. In another aspect of the present invention, the laryngoscope 14 is capable of being motion activated such that the laryngoscope 14 is powered off when no movement is detected for a predetermined period of time.

In FIG. 3, there is shown the connection assembly between the handle 16 and arm 18. At the base of the handle 16 there is a pin 46 and ball spring receptacles 48. The arm 18 is comprised of ball springs 62. To couple the arm 18 to the handle 16, the pin 46 is inserted in arm opening 47. The ball springs 62 slide into ball spring receptacles 48. This connection aligns arm plate 64 with handle plate 50 within the walls 54 of handle plate 50 such that an electrical connection is made with connectors 52.

Figure 7:
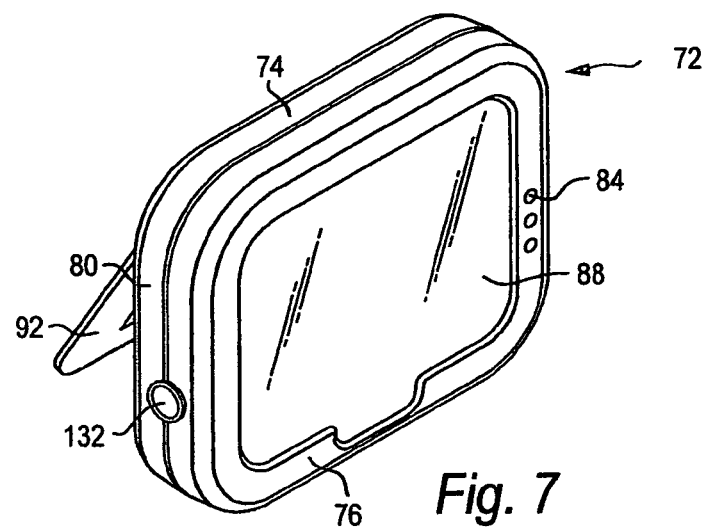
FIG. 7 is a top, front, and left side isometric view of the display unit with the stand in the open position.
Figure 8:
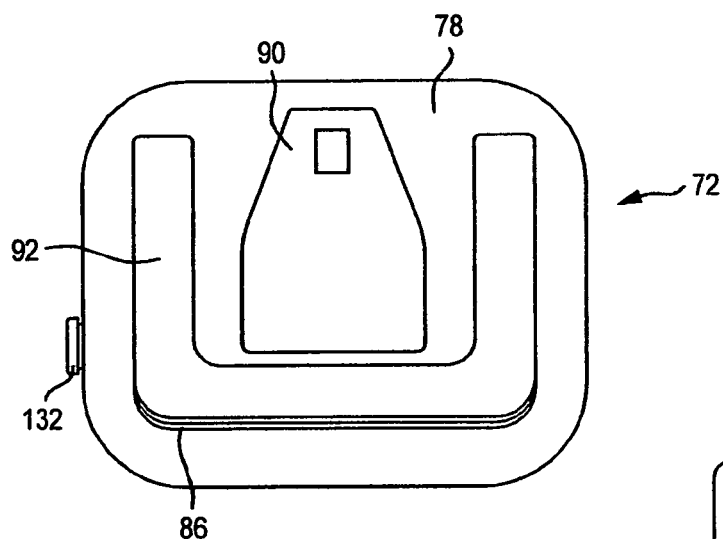
FIG. 8 is rear elevation view of the display unit with the stand in the open position.
Figure 9:
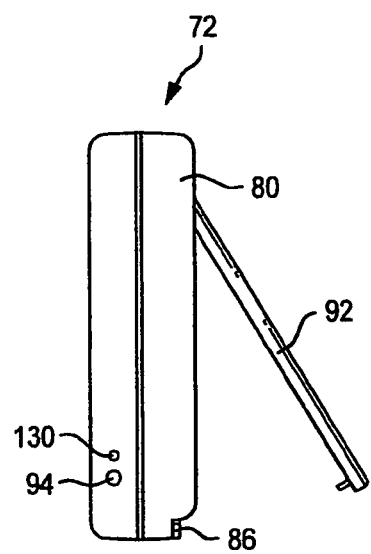
FIG. 9 is a right side isometric view of the display unit with the stand in the open position.

Referring to FIGS. 1 and 7-9, the display unit 72 is comprised of a thin container 74, a screen 88, a DC Jack 94, a battery management board and a battery. The container 74 is comprised of an IV pole attachment connector 90 such that it may be removably coupled to an IV pole attachment receiver 100 (FIG. 11) or, as shown in FIGS. 7 & 9, sit upright on a stand 92 when not attached to the IV pole attachment receiver 100. Referring to FIGS. 7-9, the container 74 of the preferred embodiment is generally rectangular and is comprised of a face 76, a back 78, and sides 80. The face 76 of the container 74 partially surrounds the screen 88 so that the screen 88 may be viewed. In the preferred embodiment, the stand 92 is pivotally coupled to the back 78 and is structured and arranged such that it extends generally rearward from the back 78 when in use and folds flat against the back 78 in a recess 86 when in the stored position. In the preferred embodiment, said recess 86 is contoured to the shape of the stand 92.

Figure 14:
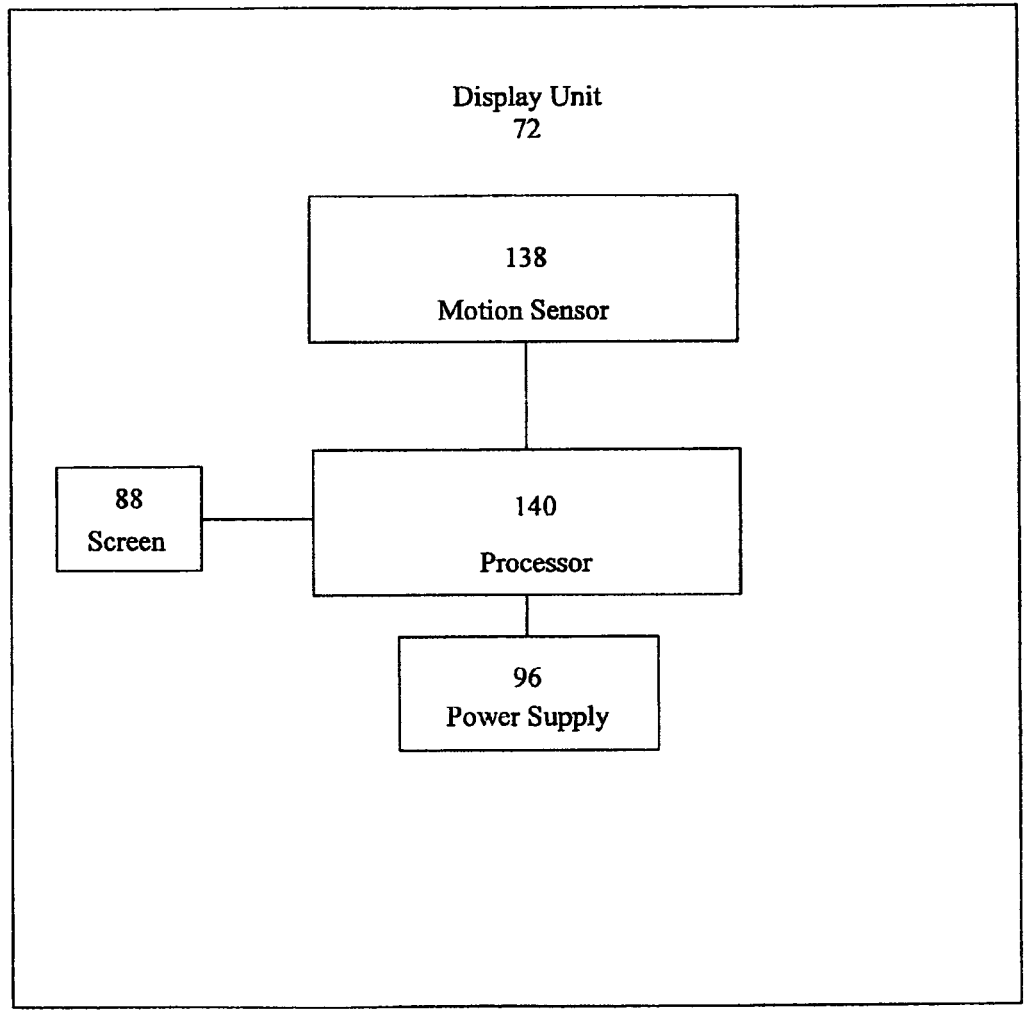
FIG. 14 is a block diagram depicting the display unit motion sensor system.

Referring to FIG. 14, in one aspect of the present invention the display unit 72 is comprised of a motion sensor 138 and processor 140 that allow the screen 88 to be motion activated such that the screen 88 is powered on upon a predetermined threshold movement. In another aspect of the present invention, the screen 88 is capable of being motion activated such that the screen 88 is powered off when no movement is detected for a predetermined period of time.

Referring again to FIGS. 7-9, in one aspect of the present invention, the face 76 has a battery status indicator 84. This indicator 84 is comprised of a plurality of LED lights. In the preferred embodiment, two green lights showing indicate to the user that the battery is fully charged and the system 12 is operable. An amber light indicates the battery is depleted and will need to be charged soon. A red light indicates the battery lacks sufficient charge to operate the screen 88, camera 22, and light 20. In the preferred embodiment, the indicator 84 is positioned at the lower portion of the face 76 near the center and beneath the screen 88.

The back 78, on the inside, has pegs and receptacles which act as coupling devices. The central pegs of the back correspond with receptacles located on the reverse side of the screen 88. The perimeter receptacles correspond with pegs located on the inside side of the face 76.

The screen 88 and battery are mounted on the inside portion of the back 78 of the container 74. The battery of the preferred embodiment is a rechargeable lithium battery and is capable of illuminating the screen 88. The screen 88 of the preferred embodiment is a 3.5 inch (Diagonal) Liquid Crystal Display (LCD). The screen 88 displays the image captured by the camera 22. In one aspect of the present invention, the screen 88 also displays other information such as the battery charge level, time, date, and the like.

The display unit 72 is further comprised of a DC input jack 94 and charge indicator 130. This jack 94 accepts the barrel portion of a charging cable. This jack 94 connects with and is used to recharge the battery. The charge indicator 130 is an LED light that, when lit, alerts the user that the battery is being charged. In one aspect of the present invention, the unit 72 may not be operated while the charge cable is inserted into the jack 94

Figure 15:
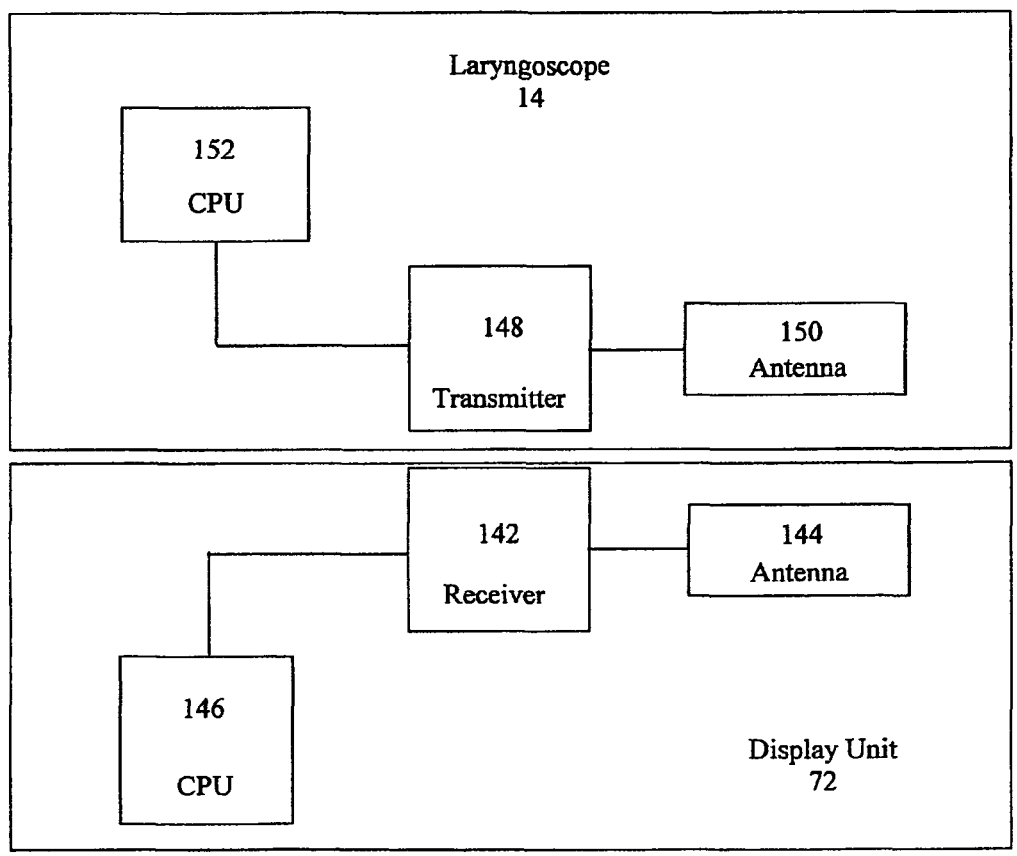
FIG. 15 is a block diagram depicting the laryngoscope and display unit wireless communication system.

The cable 62 is capable of communicating images received from the camera 22 to the screen 88 through the communication jack 132. Referring to FIG. 15, in one aspect of the present invention, the laryngoscope 14 is capable of wirelessly communicating with the display unit 72. In this embodiment, the laryngoscope 14 is further comprised of a transmitter 148, a processor or CPU 152 and an antenna 150. The display unit 72 is further comprised of a receiver 142, a processor or CPU 146 and an antenna 144. Images captured by the camera 22 are processed by the CPU 152 and transmitted wirelessly to the display unit 72 receiver 142 such that the images are displayed on screen 88.

The communication cable 96 is also capable of transmitting power generated by the battery to the light 20 and camera 22. The battery management board is a conventional and commercially available circuit board and is capable of maintaining an appropriate charge level in the battery.

The IV pole 128 is conventional and commercially available. As may be seen in FIGS. 1 and 10-11, the IV pole attachment 98 is comprised of an attachment receiver 100, an IV pole clamp 108 with a C shaped opening, a tightening screw 110 with wing knob 112, and a laryngoscope receptacle 114. The attachment receiver 100 allows the user to quickly attach and separate the display unit 72 from IV pole attachment 98 and is comprised of a bracket 102, and a quick release button 104. The attachment connector 90 of the display unit 72 may be slideably attached to the attachment receiver 100. The user may detach the display unit 72 from the attachment receiver 100 by depressing the release button 104 which activates a lever 106 that disengages the display unit 72 from the attachment receiver 100. The IV pole attachment 98 may be secured to an IV pole 128 by inserting the pole 128 in the IV clamp's 108 C shape opening and tightening the tightening screw 110 with the wing knob 112.

Figure 10:
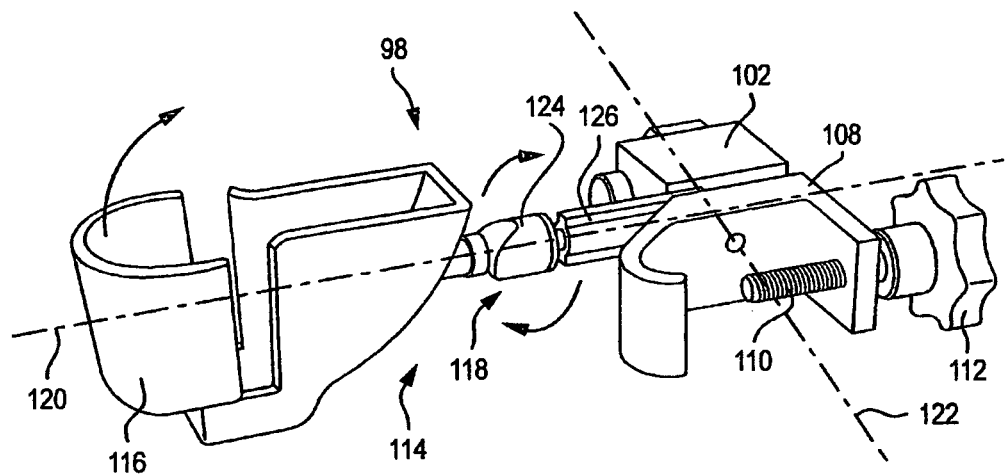
FIG. 10 is a rear isometric view of the IV pole attachment.
Figure 11:
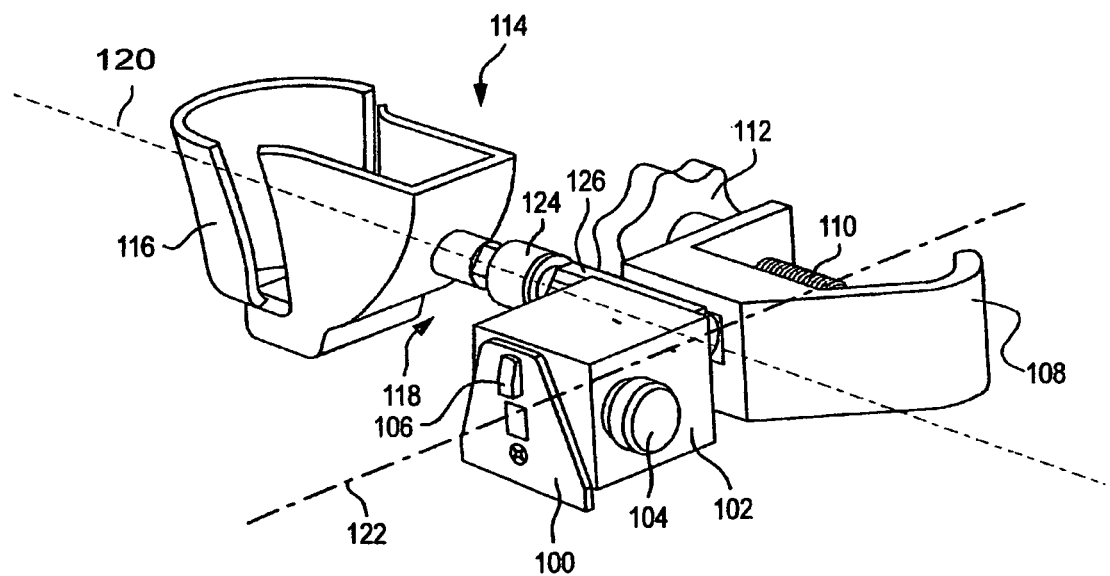
FIG. 11 is a front view of the IV pole attachment.

Referring to FIGS. 10-11, the laryngoscope receptacle 114 is comprised of a contoured holder 116 and an extension portion 118. The extension portion 118 is comprised of a first member 124 and a second member 126. In the preferred embodiment, the first member 124 is structured and arranged such that it can rotate 360 degrees around an imaginary axis 120 that extends from a longitudinal axis of the extension portion 118. The second member 126 is structured and arranged such that it can rotate up to 360 degrees around an axis 122 perpendicular to the axis 120 around which the first member 124 rotates. Therefore, as may be seen in FIGS. 10 and 11, the receptacle 114, without the need for the user detaching the IV pole attachment 98 from the IV pole 128, can be positioned on either side of an IV pole 128 and oriented such that the contoured holder 116 remains in an upright position and capable of receiving the laryngoscope 14.

The contoured holder 116 is shaped to accommodate the laryngoscope 14 in the folded position as shown in FIG. 4.

In the preferred embodiment the arm 18 is made from stainless steel. The handle 16 and container 74 are made from Acrylonitrile butadiene styrene (ABS). Although the handle 16 and container 74 of the preferred embodiment are formed from ABS, they need not be. For instance, the handle 16 and container 74 may be formed of any conventional material such as metal or plastic.

While there has been illustrated and described what is, at present, considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of this disclosure.

We claim:

1. A method of control and information processing associated with a laryngoscope, the method comprising: a. providing a user with a laryngoscope system comprising a laryngoscope and a remote control unit of said laryngoscope, said remote control unit: receiving from a laryngoscope control unit in the laryngoscope a status message directly over a wireless connection related to a status of a sensor and/or control system of said laryngoscope, notifying said user of receipt of said status message and displaying said status message on said remote control unit; b. providing by said user at said remote control unit of said laryngoscope in response to said status message a control message containing control information for controlling said laryngoscope control unit; c. delivering said control message from said remote control unit and relaying said control message to said laryngoscope control unit; d. creating a control command for said laryngoscope control unit based on the control information of the control message; and e. delivering the control command to the laryngoscope control unit.

2. The method of claim 1, comprising sending as a short message to the remote control unit a response message indicating delivery of a control command to the laryngoscope control unit.

3. The method of claim 2 wherein the response message includes status information for the laryngoscope control unit.

4. The method of claim 3 comprising controlling conditions associated with the laryngoscope using the laryngoscope control unit.

5. The method of claim 1 comprising detecting presence of an authorized person and sending said status message to the remote control unit indicating the presence of the authorized person.

6. The method of claim 5 wherein detecting the presence of the authorized person includes detecting the authorized person and authenticating a use of said system by said authorized person.

7. The method of claim 6 wherein the laryngoscope control unit includes a temperature control system, the method further comprising sending a control command to the temperature control system to adjust a temperature within the laryngoscope in response to detecting the authorized person sending said control command to the laryngoscope control unit.

8. The method of claim 7 wherein the laryngoscope control unit includes a lighting system, the method further comprising sending a control command to the lighting system to turn on lighting associated with the laryngoscope.

9. The method of claim 8 wherein the laryngoscope control unit includes a drug control system, the method further comprising sending a control command to the drug control system to dispense drugs and/or a sample associated with the laryngoscope.

10. The method of claim 1 wherein the laryngoscope control unit includes a blade control system, the method further comprising sending a control command to instruct a blade to adjust dimensions based on laryngoscope control commands associated with the laryngoscope.

11. The method of claim 1, comprising detecting a presence of an unauthorized person and sending an SMS message to the remote control unit indicating the presence of the unauthorized person.

12. The method of claim 11 wherein detecting presence of the unauthorized person includes detecting a breach of a command necessary to operate the laryngoscope and laryngoscope system.

13. The method of claim 1 wherein the laryngoscope control unit includes an error detection unit and the control command includes an instruction to bypass engaging the laryngoscope when an error is detected.

14. The method of claim 1 wherein the laryngoscope control unit includes a power control system and the control command includes an instruction to power down sensitive electronics when a fault is detected in the power control system.

15. A system for control and information processing associated with a laryngoscope, the system comprising: a laryngoscope system comprising a laryngoscope comprising laryngoscope control unit associated with the laryngoscope; a remote control unit; a controller adapted to interface with the laryngoscope control unit associated with the laryngoscope; and a wireless module adapted to: receive from the remote control unit a control message delivered from the remote control unit as a short message service message comprising control information to use for controlling the laryngoscope control unit; create control commands for the laryngoscope control unit based on the control information of the short message services message; deliver the control commands to the laryngoscope control unit via the controller; and deliver to said remote control unit for receipt as a short message services message a revised status message indicating execution of said control information; and means at the remote control unit for notifying a user of said remote control unit of said receipt and displaying information related to said revised status message.

16. The system of claim 15 wherein the wireless module is adapted to detect presence of an authorized person and to send a short message services message to the remote control unit indicating the presence of the authorized person.

17. The system of claim 15 wherein the laryngoscope control unit is adapted to control temperature and wherein the wireless module is adapted to send a control command to the temperature control system via the remote control unit to adjust a temperature associated with the laryngoscope.

18. The system of claim 15 wherein the laryngoscope control unit comprises a lighting system and wherein the wireless module is adapted to send a control command to the lighting system via the remote control unit to change a status of a lighting control command of lighting associated with the laryngoscope.

19. A method for control and information processing associated with a laryngoscope and laryngoscope system, the method comprising: a. providing a user with a laryngoscope system comprising a laryngoscope and remote control unit, said remote control unit: receiving from one or more laryngoscope control units associated with the laryngoscope a status message using short message and/or data bearer services, said status message related to the status of the laryngoscope, notifying said user of receipt of said status message and displaying said status message on said remote control unit; b. providing by said user at said remote control unit in response to said status message a control message containing control information to use for controlling said one or more laryngoscope control units; c. delivering said control message from said remote control unit to said one or more laryngoscope control units; d. creating a control command for said one or more laryngoscope control units based on the control information of the control message; and e. delivering control commands to said one or more laryngoscope control units.

20. A system for control and information processing associated with a laryngoscope and laryngoscope system, the system comprising: a laryngoscope system comprising a remote control unit and a laryngoscope including a laryngoscope control unit associated with the laryngoscope system; a controller adapted to interface with the laryngoscope control unit associated with the laryngoscope system; and a wireless module adapted to: receive from the remote control unit a control message, said control message comprising control information to use for controlling the laryngoscope control unit; create control commands for the laryngoscope control unit based on the control information; deliver the control commands to the laryngoscope control unit via the controller; and deliver to said remote control unit for receipt a revised status message indicating execution of said control information; and means at the remote control unit for notifying a user of said remote control unit of said receipt and displaying information related to said revised status message.

21. A method for control and information processing associated with a laryngoscope and laryngoscope system, the method comprising: a. providing a user with a laryngoscope system comprising a remote control unit and a laryngoscope including a laryngoscope control unit, said remote control unit: receiving through short message services message from the laryngoscope control unit a status message related to a status of the laryngoscope control unit; and notifying said user of receipt of said status message and displaying said status message on said remote control unit; b. providing by said user at said remote control unit in response to said status message a control message containing control information to use for controlling said laryngoscope control unit; c. delivering said control message from said remote control unit and relaying said control message to said laryngoscope control unit; d. creating a control command for said laryngoscope control unit based on the control information of the control message; e. delivering the control command to the laryngoscope control unit.

22. The method of claim 21 wherein the laryngoscope control unit includes a power control system and the control command includes an instruction to power down sensitive electronics when an error is detected.

23. A system for control and information processing associated with a laryngoscope system, the system comprising: a laryngoscope system comprising a remote control unit and a laryngoscope including a laryngoscope control unit associated with the laryngoscope system; a controller adapted to interface with the laryngoscope control unit associated with the laryngoscope system; and a wireless module adapted to: receive from the remote control unit a control message comprising control information to use for controlling the laryngoscope control unit; create control commands for the laryngoscope control unit based on the control information; deliver the control commands to the laryngoscope control unit via a controller; deliver to said remote control unit for receipt as a short message services message a revised status message indicating execution of said control information; and means at said remote control unit for notifying a user of said remote control unit of said receipt and displaying information related to said revised status message.

24. The system of claim 23 wherein the laryngoscope control unit includes a power control system and the wireless module is adapted to create a control command to instruct the power control system to power down sensitive electronics.

25. The system of claim 23 wherein the laryngoscope control unit includes a temperature control system and wherein the wireless module is adapted to create a control command to instruct the temperature system.

26. The system of claim 23 wherein the laryngoscope control unit includes a drug control system and wherein the wireless module is adapted to create a control command to instruct the drug control system.

27. The system of claim 23, wherein the laryngoscope control unit includes a blade control system and wherein the wireless module is adapted to create a control command to instruct the blade control system.

28. A method for control and information processing associated with a laryngoscope system, the method comprising: a. providing a user with a laryngoscope system comprising remote control unit and a laryngoscope including a laryngoscope control unit, said remote control unit: receiving through short message services message from the laryngoscope control unit a status message including a status of the laryngoscope control unit; and notifying said user of receipt of said status message and displaying said status message on said remote control unit; b. providing by said user at said remote control unit in response to said status message a control message containing control information to use for controlling said laryngoscope control unit; c. delivering said control message from said remote control unit as a short message services message and relaying said control message to said laryngoscope control unit; d. creating a control command for said laryngoscope control unit based on the control information of the control message; e. delivering the control command to the laryngoscope control unit.

29. The method of claim 28 wherein the laryngoscope control unit includes a temperature system and the control command includes an instruction to adjust temperature.

\* \* \* \* \*